(12) United States Patent
Pedrozo

(10) Patent No.: US 10,434,217 B2
(45) Date of Patent: *Oct. 8, 2019

(54) BONE INDUCTION SYSTEM AND METHODS

(71) Applicant: Vivex Biomedical Inc., Marietta, GA (US)

(72) Inventor: Hugo Pedrozo, Austin, TX (US)

(73) Assignee: Vivex Biologics Group, Inc., Atlanta, GA (US)

(*) Notice: Subject to any disclaimer, the term of this patent is extended or adjusted under 35 U.S.C. 154(b) by 266 days.

This patent is subject to a terminal disclaimer.

(21) Appl. No.: 15/082,586

(22) Filed: Mar. 28, 2016

(65) Prior Publication Data

US 2016/0206782 A1 Jul. 21, 2016

Related U.S. Application Data

(62) Division of application No. 12/338,659, filed on Dec. 18, 2008, now Pat. No. 9,320,761.

(51) Int. Cl.
| | |
|---|---|
| A61K 38/18 | (2006.01) |
| A61K 35/28 | (2015.01) |
| A61K 35/14 | (2015.01) |
| A61L 27/36 | (2006.01) |
| A61L 27/54 | (2006.01) |
| A61L 27/58 | (2006.01) |

(52) U.S. Cl.
CPC ......... *A61L 27/3608* (2013.01); *A61K 35/14* (2013.01); *A61K 35/28* (2013.01); *A61K 38/18* (2013.01); *A61L 27/365* (2013.01); *A61L 27/3616* (2013.01); *A61L 27/3687* (2013.01); *A61L 27/3691* (2013.01); *A61L 27/54* (2013.01); *A61L 27/58* (2013.01); *A61L 2300/414* (2013.01); *A61L 2300/45* (2013.01); *A61L 2430/02* (2013.01); *A61L 2430/34* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 5,236,456 | A | 8/1993 | OLeary et al. |
| 5,490,937 | A | 2/1996 | Van Reis |
| 6,919,308 | B2 | 7/2005 | Oppermann et al. |
| 6,949,251 | B2 | 9/2005 | Dalal et al. |
| 7,041,641 | B2 | 5/2006 | Rueger et al. |
| 7,132,110 | B2 | 11/2006 | Kay et al. |
| 7,172,629 | B2 | 2/2007 | McKay |
| 7,189,392 | B1 | 3/2007 | Kim et al. |
| 7,847,072 | B2 | 12/2010 | Thorne |
| 2002/0082697 | A1 | 6/2002 | Damien |
| 2003/0185803 | A1 | 10/2003 | Kadiyala |

(Continued)

OTHER PUBLICATIONS

Liu et al., Platelets, 2003, vol. 14(4):233-237.*
(Continued)

*Primary Examiner* — Xiaozhen Xie
(74) *Attorney, Agent, or Firm* — David L. King

(57) ABSTRACT

An osteogenic composition suitable for use in bone and soft tissue reparative procedures is provided for herein. Methods for preparing osteogenic composition from blood and bone marrow are also provided for. The osteogenic compositions contain therapeutically effective concentrations of one or more osteogenic agents such as BMP-2, TGF-β, PDGF and VEGF.

24 Claims, 5 Drawing Sheets

(56) References Cited

U.S. PATENT DOCUMENTS

| | | |
|---|---|---|
| 2004/0072322 A1 | 4/2004 | Thorne |
| 2005/0205498 A1 | 9/2005 | Sowemimo-Coker |
| 2006/0004189 A1* | 1/2006 | Gandy .................. C07K 14/475 530/399 |
| 2006/0246150 A1 | 11/2006 | Thorne |
| 2007/0003593 A1 | 1/2007 | Wironen et al. |
| 2007/0049739 A1 | 3/2007 | Troxel et al. |
| 2007/0249815 A1* | 10/2007 | Thorne .................... C07K 1/34 530/414 |

OTHER PUBLICATIONS

Chua et al., J. Cell. Physiol., 1983, vol. 117(1):116-122.*
Korf-Klingebiel et al., Eur. Heart J., 2008, vol. 29(2):2851-2858; Epub Oct. 25, 2008.*
Roukis et al., Adv. Ther., 2006, vol. 23(2):218-237.*
Chua, Chu Chang; Geiman, Deborah and Ladda, Roger L; Transforming Growth Factors Released From Kirsten Sarcoma Virus Transformed Cells Do Not Compete for Epidermal Growth Factor Membrane Receptors; Journal of Cellular Physiology 17:116;-122 (1983).
L1-L4, Feb. 8, 2012.
Liu, Yawei, Kalen, Anders; Risto, Olof; Wahlstrom, Ola; Time- and pH-dependent release of PDGF and TGF-B from platelets in vitro; Platelets (Jun. 2003) 14(4), 233-237.
Buffer Reference Center, Sigma-Aldrich, http://www.sigmaaldrich.com/life-science/core-bioreagents/biological-buffers/learning-ce . . . Nov. 26, 2012.
East Search History, document 1-2, Nov. 26, 2012; Feb. 8, 2012.
L1-L4, Feb. 8, 2012.
Platelet Transfusion—Standard of Care; http://www.standardofcare.com/mwiki/index.php?title=Platelet transfusion; Feb. 8, 2012.

* cited by examiner

BONE INDUCTION SYSTEM AND METHODS

RELATED APPLICATIONS

The present invention is a division of U.S. application Ser. No. 12/338,659 filed on Dec. 18, 2008, now U.S. Pat. No. 9,320,761 issued Apr. 26, 2016 entitled, "Bone Induction System And Methods".

FIELD OF THE INVENTION

The present invention generally relates to a bone induction system suitable for use in reparative therapies and methods of making same. More specifically, the invention relates to methods for preparing osteogenic compositions from blood and bone marrow.

BACKGROUND OF THE INVENTION

A variety of osteogenic proteins have been shown to induce either cartilage or bone formation in vivo. For example, BMP-2 has been found to be safe and feasible for use in the treatment of fractures and for use in bone regeneration. Certain recombinant osteogenic proteins have also been extensively studied and have demonstrated significant osteogenic activity in several models of bone formation.

The therapeutic utility of BMP-2 and other osteogenic proteins is widely recognized. It is contemplated that the availability of the pure BMP-2 protein would revolutionize orthopedic medicine, certain types of plastic surgery, and various periodontal and craniofacial reconstructive procedures.

Currently, there are two major methods for the production of osteogenic proteins. The first involves extracting osteogenic proteins from demineralized cortical bone. The second method involves expressing osteogenic proteins using a recombinant expression system, and isolating the recombinant protein.

Both methods of production have significant drawbacks. The first method of purifying osteogenic proteins from bone is costly, time-consuming, and generally produces low yield. The second method enables production of osteogenic proteins with higher yield, but obtaining therapeutic amounts of recombinant proteins may be cost prohibitive in certain situations.

Furthermore, recombinant systems may lack additional factors that are present in tissue-derived protein preparations.

There exists a need for preparing osteogenic protein preparations, which combines the benefit of high yield and activity and minimizing cost.

U.S. Pat. No. 7,172,629 to McKay describes osteogenic paste compositions with enhanced osteoinductive properties for use in bone repair. The composition include a resorbable paste carrier, a more slowly resorbed mineral matrix, and Bone Morphogenetic Protein (BMP) or other osteogenic factor, which enable increased osteoinductive activity while retaining a scaffold for the formation of new bone at the implant site. Methods for making and methods for therapeutic use of the compositions are also described.

U.S. Pat. No. 5,236,456 to O'Leary et al. describes osteogenic compositions obtained from demineralized bone tissue. The osteogenic composition is compatible with many types of materials which can be introduced in the composition to enhance or augment bone repair or reconstruction. O'Leary further contemplates the addition of demineralized bone powder and other osteogenic, osteoinductive and/or osteoconductive substances such as bone morphogenic proteins (BMP) and/or any of numerous other medically useful substances to the osteogenic composition.

U.S. Pat. No. 7,132,110 to Kay et al. describes osteogenic compositions prepared by a process including the steps of subjecting demineralized bone to an extraction medium to produce an insoluble extraction product and a soluble extraction product, separating the insoluble extraction product and the soluble extraction product, drying the soluble extraction product to remove all or substantially all of the moisture in the soluble extraction product, and combining the dried soluble extraction product of step c) with demineralized bone particles.

U.S. Pat. No. 7,189,392 to Kim et al. describes an injectable formulation for delivery of osteogenic proteins. The formulation comprises a pharmaceutically acceptable admixture of an osteogenic protein; and formulations comprising osteogenic protein, hyaluronic acid derivatives and tricalcium phosphate. Methods for formulating porous injectable gels and pastes from hyaluronic acid are also disclosed.

U.S. Pat. No. 7,041,641 to Rueger et al. describes osteogenic devices and uses thereof for repair of bone and cartilage defects. The devices and methods promote formation of repair tissue with using less osteogenic protein than other devices. Defects repairable with the devices include critical size defects, non-critical size defects, non-union fractures, fractures, osteochondral defects, subchondral defects, and defects resulting from degenerative diseases such as osteochondritis dissecans.

U.S. Pat. No. 6,949,251 to Dalal et al. describes a porous a porous β-tricalcium phosphate material for bone implantation. The pore size diameter is in the range of 20-500 μm. The porous β-TCP material provides a carrier matrix for bioactive agents and can form a moldable putty composition upon the addition of a binder. Preferably, the bioactive agent is encapsulated in a biodegradable agent. Dalal also describes a kit and an implant device comprising the porous β-TCP, and a bioactive agent and a binder. The invention also provides an implantable prosthetic device comprising a prosthetic implant having a surface region, a porous β-TCP material disposed on the surface region and optionally comprising at least a bioactive agent or a binder. Methods of producing the porous β-TCP material and inducing bone formation are also provided.

U.S. Pat. No. 6,919,308 to Oppermann et al. describes osteogenic devices comprising a matrix containing substantially pure natural-sourced mammalian osteogenic protein; DNA and amino acid sequences for novel polypeptide chains useful as subunits of dimeric osteogenic proteins; vectors carrying sequences encoding these novel polypeptide chains and host cells transfected with these vectors; methods of producing these polypeptide chains using recombinant DNA technology; antibodies specific for these novel polypeptide chains; osteogenic devices comprising these recombinant proteins in association with an appropriate carrier matrix; and methods of using the osteogenic devices to mimic the natural course of endochondral bone formation in mammals.

U.S. patent publication No. 20070003593 by Wironen et al. describes an orthopedic bone paste useful for the repair of non-union fractures, periodontal ridge augmentation, craniofacial surgery, implant fixation, impaction grafting, or any other procedure in which generation of new bone is deemed necessary. The orthopedic composition comprises an osteogenic compound in a gelatin matrix. The osteogenic compound may include demineralized bone matrix (DBM), bioactive glass ceramic, bioactive ceramic, calcium phosphate ceramic, hydroxyapatite, hydroxyapatite carbonate, corraline hydroxyapatite, calcined bone, tricalcium phosphate, or like material. The composition may further include bone morphogenetic protein, TGF-, PDGF, or mixtures thereof.

U.S. patent publication No. 20040072322 by Thorne describes methods for purifying osteogenic proteins from calcified bone. The method includes a demineralization process, a protein extraction process, a high molecular weight ultrafiltration process, a low molecular weight ultrafiltration process, and a recovery process. The high and low ultrafiltration processes preferably select proteins having a nominal molecular weight between approximately 8 kilodaltons and approximately 50 kilodaltons. Processes of the present invention may be used to recover osteogenic proteins from bone demineralization waste streams.

U.S. patent publication No. 20050205498 by Sowemimo-Coker describes methods and compositions prepared from a cell concentrate, such as, for example, an osteogenic cell concentrate, from a physiological solution, such as bone marrow aspirate, blood, or a mixture thereof. The invention also provides methods and compositions utilizing two physiological solution-processing techniques, particularly in a point of care environment, wherein centrifugation is not employed.

U.S. patent publication No. 20060246150 by Thorne describes a composition for the induction of bone growth. The composition includes a substrate, bone growth protein; and sources of calcium and phosphate. The composition is acidic, which promotes high activity of the bone growth protein. The calcium and phosphate sources can be provided as an acidic calcium phosphate salt. Also disclosed are methods of the making the composition and methods of using it.

U.S. patent publication No. 20030185803 by Kadiyala describes a musculoskeletogenic MSG graft composite made from whole bone marrow aspirate (BMA) having native levels of musculoskeletal progenitor cells MSPCs. The composite includes a suspension of fractionated BMA comprising MSPCs present at a level greater than their native level in whole BMA, and red blood cells (RBCs) present at a level less than their native level in whole BMA, and a porous sterile matrix having an average pore size of at least 20 μm.

U.S. patent publication No. 20020082697 by Damien describes collagen-based osteogenic materials having useful shaping and handling properties and which are easier for health care practitioners to use than conventional implantable osteogenic materials. The shaped implantable compositions or devices also provide a suitable matrix for the release of osteogenic substances and other desirable biologically active agents at the site of implantation to promote bone growth.

The aforementioned prior art references are incorporated by reference as though fully set forth herein.

SUMMARY OF THE INVENTION

In one embodiment, a method of preparing an osteogenic composition may include obtaining from a subject a biological sample containing one or more osteogenic agents. In an embodiment, a biological sample may include a blood sample. In another embodiment, a biological sample may include a bone marrow aspirate. A lysate may be prepared from the biological sample. The lysate may include solid material and one or more osteogenic agents. In an embodiment, a lysate may be separated into at least a first and second fraction such that the solid material is contained in one fraction, and the one or more osteogenic agents are contained in a another fraction. In one embodiment, separating the lysate may include passing the lysate through a hollow fiber membrane filtration system such that the filtrate contains the osteogenic agents, and the retentate contains the solid material. The membrane of the filtration system may have an average pore size of between about 0.2 to about 5 microns. In another embodiment, separating the lysate may include centrifuging the lysate so that the osteogenic agents are contained in the supernatant, and the pellet contains solid material. The osteogenic agents prepared from the biological sample may be concentrated. Concentrating the osteogenic agents may include applying the fraction in which they are contained to a hollow fiber membrane system. In an embodiment, the concentrated fraction may be applied to a pharmaceutical carrier system suitable for use in bone and soft tissue therapies.

In another embodiment, a method of preparing an osteogenic composition may include obtaining a blood sample from a subject. In an embodiment, a preparation enriched for red blood cells may be prepared from the blood sample. A lysate may be prepared from the blood sample or the enriched preparation. The lysate includes solid material and one or more osteogenic agents. In an embodiment, a lysate may be subjected to a separating step such that the solid material is contained in one fraction, and the one or more osteogenic agents are contained in another fraction. In one embodiment, separating the lysate may include passing the lysate through a hollow fiber membrane filtration system such that the filtrate contains the osteogenic agents, and the retentate contains the solid material. The membrane of the filtration system may have an average pore size of between about 0.2 to about 5 microns. In another embodiment, separating the lysate may include centrifuging the lysate so that the osteogenic agents are contained in the supernatant, and the pellet contains solid material. The osteogenic agents prepared from the blood sample may be concentrated. Concentrating the osteogenic agents may include applying the fraction in which they are contained to a tangential flow hollow fiber membrane system. In an embodiment, the concentrated fraction may be applied to a pharmaceutical carrier system suitable for use in bone and soft tissue therapies.

In another embodiment, a method of preparing an osteogenic composition may include obtaining a bone marrow aspirate from a subject. The cells in the aspirate may be dispersed and a lysate containing solid material and one or more osteogenic agents present in the aspirate may be prepared therefrom. In an embodiment, the lysate may be separated into at least a first and a second fraction such that the solid material is contained in one fraction, and the osteogenic agents are contained in another fraction. In one embodiment, separating the lysate may include passing the lysate through a tangential flow hollow fiber membrane filtration system such that the filtrate contains the osteogenic agents, and the retentate contains the solid material. The membrane of the filtration system may have an average pore size of between about 0.2 to about 5 microns. In another embodiment, separating the lysate may include centrifuging the lysate so that the osteogenic agents are contained in the supernatant, and the pellet contains solid material. The osteogenic agents prepared from the bone marrow sample may be concentrated. Concentrating the osteogenic agents may include applying the fraction in which they are contained to a hollow fiber membrane system. In an embodiment, the concentrated fraction may be applied to a pharmaceutical carrier system suitable for use in bone and soft tissue therapies.

In another embodiment, a method of preparing an autologous bone induction system (ABIS) containing an osteogenic composition may include obtaining a bone marrow aspirate from a subject. The cells in the aspirate may be dispersed and the cells in the dispersed aspirate may be separated from the solid material present in the aspirate. In one embodiment, at least a portion of the cells may be collected from the aspirate. The cells may be collected by passing the aspirate through a hollow fiber membrane system having an average pore size of 30 to 80 nm. In an embodiment, a first portion of the collected cells may be set aside and a dispersion prepared from a second portion of the collected cells. A lysate may be prepared from the second portion. In an embodiment, the lysate may be separated into two or more fraction such that the solid material is contained in one fraction, and the osteogenic agents are contained in another fraction.

In one embodiment, separating the lysate may include passing the lysate through a tangential flow hollow fiber membrane filtration system such that the filtrate contains the osteogenic agents, and the retentate contains the solid material. The membrane of the filtration system may have an average pore size of between about 0.2 to about 5 microns. In another embodiment, separating the lysate may include centrifuging the lysate so that the osteogenic agents are contained in the supernatant, and the pellet contains solid material. The osteogenic agents prepared from the bone marrow sample may be concentrated. Concentrating the osteogenic agents may include applying the fraction in which they are contained to a hollow fiber membrane system. In an embodiment, the concentrated osteogenic factor preparation may be combined with the first portion of the cells set aside after the separating step to produce an autologous bone induction system. In an embodiment, the autologous bone induction system may be applied to a pharmaceutical carrier system suitable for use in bone and soft tissue therapies.

Osteogenic compositions produced in accordance with the embodiments described herein can typically be prepared in less than 2 hours, more preferably less than 1 hour, and most preferably less than 30 minutes, thus allowing their preparation and use in a point of care setting.

In some embodiments, a suitable pharmaceutical carrier medium may include a synthetic material, a natural material, or both. In some embodiments, a pharmaceutical carrier medium may include biocompatible material that facilitates, permits, or enhances the laying down of new bone matrix, bone growth and/or bone ingrowth. A pharmaceutical carrier medium may include ceramics, such as calcium sulfate or calcium phosphate, polymers, metals, allograft bone, autograft bone, demineralized bone matrix, or any mixture thereof In some embodiments, a pharmaceutical carrier medium may be in the form of a block, paste, cement, powder, granule, putty, gel, or so forth. In certain embodiments, a pharmaceutical carrier medium may breaks down over time when placed in the body. A pharmaceutical carrier medium may be a dust, powder, granule, chip, putty, tablet, mixture thereof.

In some embodiments, a pharmaceutical carrier medium may be in the form of a paste, which is delivered to a tissue in a subject having need thereof. The paste may substantially harden over time. The paste may include ceramics, such as calcium sulfate or calcium phosphate, polymers, metals, allograft bone, autograft bone, demineralized bone matrix, or any mixture thereof. In an embodiment, an osteogenic composition may be mixed with the paste such that the composition is evenly distributed in the paste. In an alternate embodiment, an osteogenic composition may be applied to a surface of the paste and absorbed therein. In yet a further embodiment, the paste may be applied to a bone, and the osteogenic composition is applied in situ.

In some embodiments, a pharmaceutical carrier medium may be substantially solid. At least a portion of the solid carrier medium may be porous. The solid carrier medium may have any shape. The solid carrier medium may include ceramics, such as calcium sulfate or calcium phosphate, polymers, metals, allograft bone, autograft bone, demineralized bone matrix, or any mixture thereof. In an embodiment, an osteogenic composition may be applied to the surface the solid carrier medium and be absorbed therein. In an alternate embodiment, the solid carrier medium may be soaked in a solution containing the osteogenic composition. In a further alternate embodiment, an osteogenic composition may be applied to a solid carrier medium using pressure.

BRIEF DESCRIPTION OF THE DRAWINGS

Other objects and advantages of the invention will become apparent upon reading the following detailed description and upon reference to the accompanying drawings in which.

Figure 1:
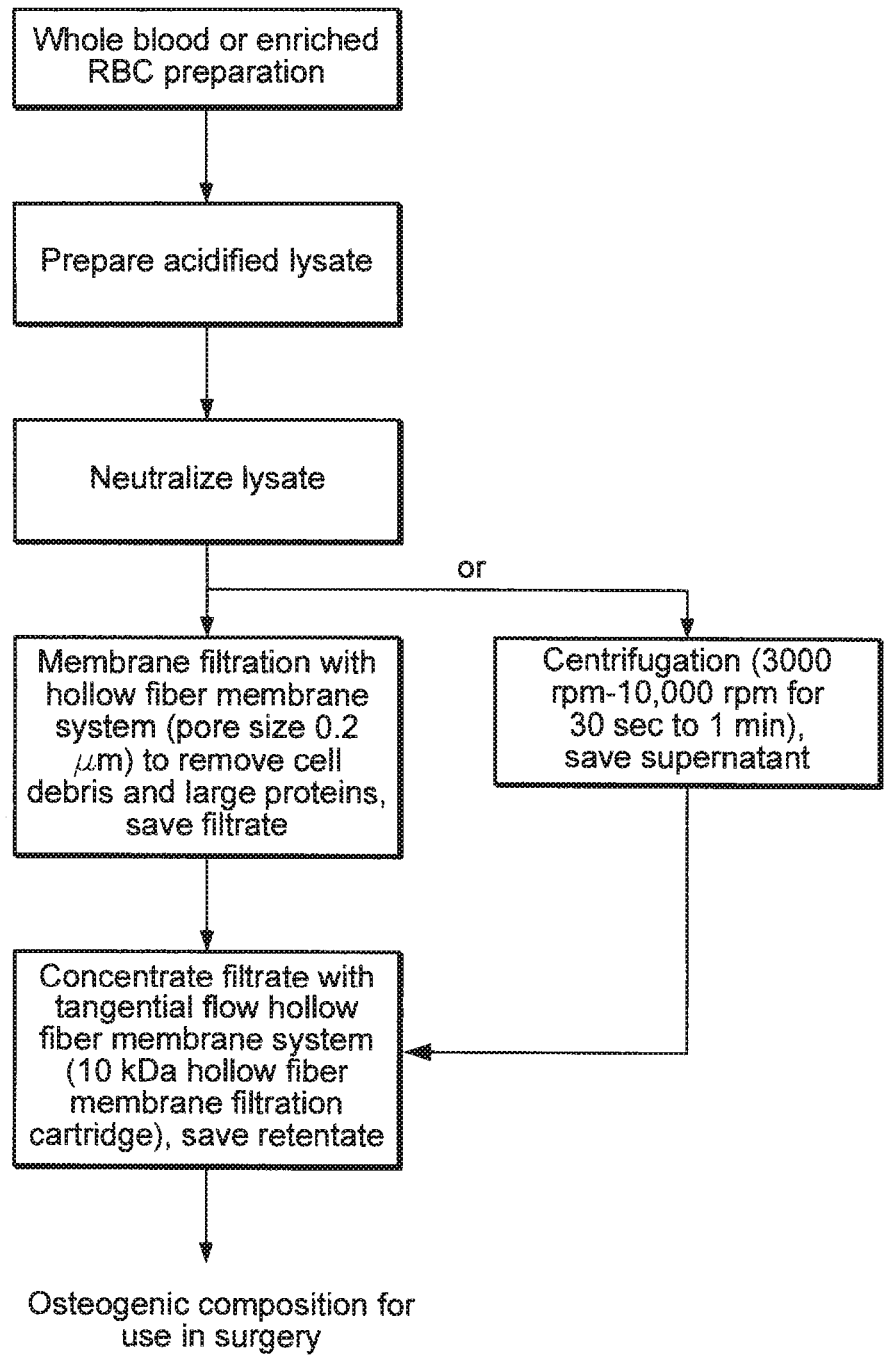
FIG. 1 is a flow chart depicting a method of preparing a osteogenic preparation from a blood sample.

While the invention is susceptible to various modifications and alternative forms, specific embodiments thereof are shown by way of example in the drawings and will herein be described in detail. It should be understood, however, that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Definitions

The terms used throughout this specification generally have their ordinary meanings in the art, within the context of the invention, and in the specific context where each term is used. Certain terms are discussed below, or elsewhere in the specification, to provide additional guidance to the practitioner in describing the various embodiments of the invention and how to make and use them. It will be appreciated that the same thing can be said in more than one way.

Consequently, alternative language and synonyms may be used for any one or more of the terms discussed herein, nor is any special significance to be placed upon whether or not a term is elaborated or discussed in greater detail herein. Synonyms for certain terms may be provided. A recital of one or more synonyms does not exclude the use of other synonyms. The use of examples anywhere in this specification, including examples of any terms discussed herein, is illustrative only, and in no way limits the scope and meaning of the invention or of any exemplified term.

As used herein, terms such as "pharmaceutical carrier," "pharmaceutical composition," "pharmaceutical formulation," "pharmaceutical preparation," or the like, generally refer to formulations that are adapted to deliver a prescribed dosage of one or more pharmacologically active compounds to a cell, a group of cells, an organ or tissue, an animal or a human. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release," "controlled release," or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

The term "bone marrow" as used herein refers to soft, gelatinous tissue that fills bone cavities. It is comprised of red bone marrow, which comprises stem cells, progenitor cells, precursor cells, and functional blood cells, and yellow bone marrow, which mainly stores fats.

The term "bone marrow aspirate" as used herein refers to the material obtained upon aspirating bone marrow from a bone, such as by needle.

The term "centrifugation" as used herein refers to the rotation in a compartment of an apparatus, said compartment spun about an axis for the purpose of separating materials.

The term "concentrate" as used herein refers to a composition that comprises a greater concentration of a specific component, for example, a particulate or particulates, compared to a parent source.

The term "retentate" as used herein refers to the material that is retained by a filter upon passage of a multiphasic solution across the filter.

The term "filtrate" as used herein refers to material that passes through a permeable filter upon passage of a multiphasic solution across the filter.

The term "filtration" as used herein refers to the process of passing a liquid comprising particular matter through a porous material for the purpose of separating the liquid from at least some of the particular matter, for separating some particular matter from other particular matter, or both.

As used herein the terms "subject" generally refers to a mammal, and in particular to a human.

Terms such as "in need of treatment," "in need thereof," "who would benefit from such treatment" and the like, when used in the context of administering a pharmaceutical preparation to a subject, generally refers to a judgment made by an appropriate healthcare provider that an individual or animal requires or will benefit from a specified treatment or medical intervention.

Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

The phrases "therapeutically effective amount" and "effective amount" are synonymous unless otherwise indicated, and mean an amount of a compound of the present invention that is sufficient to improve the condition, disease, or disorder being treated. Determination of a therapeutically effective amount, as well as other factors related to effective administration of a compound of the present invention to a patient in need of treatment, including dosage forms, routes of administration, and frequency of dosing, may depend upon the particulars of the condition that is encountered, including the patient and condition being treated, the severity of the condition in a particular patient, the particular compound being employed, the particular route of administration being employed, the frequency of dosing, and the particular formulation being employed. Determination of a therapeutically effective treatment regimen for a patient is within the level of ordinary skill in the medical or veterinarian arts. In clinical use, an effective amount may be the amount that is recommended by the U.S. Food and Drug Administration, or an equivalent foreign agency. The amount of active ingredient that can be combined with the carrier materials to produce a single dosage form varies depending upon the mammalian host treated and the particular mode of administration.

The term "pharmacologically inert," as used herein, generally refers to a compound, additive, excipient, binder, vehicle, and the like, that is substantially free of any pharmacologic or "drug-like" activity.

The term "pharmaceutical carrier medium" as used herein refers to a material that can be admixed with an osteogenic preparation and that that facilitates bone growth upon administration to a bone defect with. A pharmaceutical carrier medium may be comprised of a synthetic material, a natural material, or both. In some embodiments, a pharmaceutical carrier medium is comprised of biocompatible material that facilitates, permits, or enhances the laying down of new bone matrix, bone growth and/or bone ingrowth. A pharmaceutical carrier medium may include ceramics, such as calcium sulfate or calcium phosphate, a polymer, a metal, allograft bone, autograft bone, demineralized bone matrix, a mixture thereof, and so forth. In more specific embodiments, a pharmaceutical carrier medium may be a block, paste, cement, powder, granule, putty, gel, or so forth. In certain embodiments, a pharmaceutical carrier medium may breaks down over time when placed in the body. A pharmaceutical carrier medium may be a dust, powder, granule, chip, putty, tablet, mixture thereof, and so forth.

As used herein, a composition that is referred to as being "physiologically acceptable" is a composition that is non-toxic, biocompatible and whose physical and chemical features (e.g., pH, osmolarity, temperature, and the like) fall within a range that is substantially unlikely to induce or be the cause of adverse physiological responses (e.g., inflammation, hypersensitivity, toxicity, and the like). A "physiologically acceptable" aqueous solution will typically have a pH in the range of about 6.0 to about 8.5, in the range of about 7.0 to 8.0, or in the range of about 7.2 to about 7.6. Such a solution will typically have an osmolarity in the range of about 200 to about 500 mOsmol/L, about 250 to about 350 mOsmol/L or about 280 to about 310 mOsmol/L. Thus the term "physiological acceptable salts" is generally meant to encompass those salts, as well as aqueous solutions made therefrom, having the chemical and biological properties described above.

The term "osteogenic" as used herein refers to a material that stimulates growth of new bone tissue.

A preparation containing "osteogenic factors" generally refers to a composition that can be used to induce and/or support the formation, development and growth of new bone, and/or the remodeling of existing bone. An "osteogenic agent," as used herein, is an agent that can elicit, facilitate and/or maintain the formation and growth of bone tissue. Many osteogenic agents function, at least in part, by stimulating or otherwise regulating the activity of osteoblast and/or osteoclasts. Exemplary osteogenic agents include certain polypeptide growth factors, such as, osteogenin, Insulin-like Growth Factor (IGF)-1, IGF-II, TGF-$\beta$1, TGF-$\beta$2, TGF-$\beta$3, TGF-$\beta$4, TGF-$\beta$5, osteoinductive factor (OIF), basic Fibroblast Growth Factor (bFGF), acidic Fibroblast Growth Factor (aFGF), Platelet-Derived Growth Factor (PDGF), vascular endothelial growth factor (VEGF), Growth Hormone (GH), growth and differentiation factors (GDF)-5 through 9, osteogenic protein-I (OP-1) and any one of the many known bone morphogenic proteins (BMPs), including but not limited to BMP-1, BMP-2, BMP-2A, BMP-2B, BMP-3, BMP-3b, BMP-4, BMP-5, BMP-6, BMP-7, BMP-8, BMP-8b, BMP-9, BMP-10, BMP-11, BMP-12, BMP-13, BMP-14, BMP-15. An osteogenic composition may include one or more agents that support the formation, development and growth of new bone, and/or the remodeling thereof. Typical examples of compounds that function in such a supportive manner include, though are not limited to, extracellular matrix-associated bone proteins (e.g., alkaline phosphatase, osteocalcin, bone sialoprotein (BSP) and osteocalcin in secreted phosphoprotein (SPP)-1, type I collagen, fibronectin, osteonectin, thrombospondin, matrix-gla-protein, SPARC, alkaline phosphatase and osteopontin).

A preparation containing one or more osteogenic factors may be referred to herein as an "osteogenic composition."

As used herein, the term "growth factor" generally refers to a factor, typically a polypeptide, that affects some aspect of the growth and/or differentiation of cells, tissues, organs, or organisms.

As used herein, the term "bone morphogenic protein," or "BMP" generally refers to a group of polypeptide growth factors belonging to the TGF-$\beta$ superfamily. BMPs are widely expressed in many tissues, though many function, at least in part, by influencing the formation, maintenance, structure or remodeling of bone or other calcified tissues. Members of the BMP family are potentially useful as therapeutics. For example, BMP-2 has been shown in clinical studies to be of use in the treatment of a variety of bone-related conditions.

As used herein, the term "bone protein" generally refers to a polypeptide factor that supports the growth, remodeling, mineralization or maintenance of calcified tissues. Bone proteins are typically components of, or associate with cells and structures that form extracellular matrix structures. Typical examples of bone proteins may include, though are not limited to, alkaline phosphatase, osteocalcin, bone sialoprotein (BSP) and osteocalcin in secreted phosphoprotein (SPP)-1, type I collagen, type IV collagen, fibronectin, osteonectin, thrombospondin, matrix-gla-protein, SPARC, alkaline phosphatase and osteopontin.

As used herein, the term "antibiotic" generally refers to a naturally occurring, synthetic or semi-synthetic chemical substance that is derivable from a mold or bacterium that, when diluted in an aqueous medium, kills or inhibits the growth of microorganisms and can cure or treat infection.

As used herein, the term "analgesic" is used in reference to a pharmacologically active agent or composition that alleviates pain without causing loss of consciousness As used herein, the term "recombinant," when used in reference to a polypeptide, generally refers to a protein, or a fragment thereof, that is made and/or at least partially purified using recombinant DNA technology. Techniques for the production of recombinant proteins are widely known in the art. Briefly, a nucleotide sequence encoding the portion of the protein that is to be expressed is inserted in frame to an expression vector (e.g., a viral, bacterial, fungal, yeast, plant, insect or mammalian expression vector) and said expression vector is introduced into an appropriate cell system in culture. The recombinant protein produced by cultured cells may be at least partially purified using a variety of techniques. General guidance in techniques used for the production of recombinant proteins may be found, for example, in Sambrook, J. et al. Molecular Cloning: A Laboratory Manual. 2nd, Ed., Cold Spring Harbor Laboratory, Cold Spring Harbor Laboratory Press, Cold Spring Harbor, N.Y., 1989, which is incorporated herein by reference.

As used herein, the term "at least partially purified" when used in the context of a polypeptide or a composition containing a polypeptide, generally refers to an expressed polypeptide that is substantially free of other cellular material, or culture medium that was present during the production thereof.

The term "autologous bone marrow" generally refers to a bone marrow aspirate derived from a substantially genetically identical reference source (i.e., the same subject or a genetic clone thereof). Typically, the term refers to a bone marrow sample derived from bone of the same subject in which the material will ultimately be used.

The term "hollow fiber filtration system" as used herein refers to a filtration device comprising a hollow tubular outer covering, wherein inside the hollow tubular outer covering there are individual tubes whose walls are filters; the individual tubes lay in a direction parallel to the length of the tube. In specific embodiments, the direction of feed of a product through a device is perpendicular to the direction of flow across the membrane. In some embodiments it generally comprises tangential flow filtration, which regards the recirculation of a retentate across the surface of the membrane filter. In alternative embodiments, there is no tangential flow filtration.

The system and methods set forth herein describe osteogenic compositions prepared from a biological sample obtained from a subject, as well as methods for preparing same. Osteogenic compositions produced in accordance with the embodiments described herein can typically be prepared in less than 2 hours, more preferably less than 1 hour, and most preferably less than 30 minutes, thus allowing their preparation and use in a point of care setting.

The osteogenic compositions made in accordance with the embodiments described herein contain various osteogenic factors, including but limited to one or more BMPs, TGFs, VEGF and PDGF. Osteogenic compositions prepared in accordance with the following methods are prepared from one or more biological samples obtained from a subject who is undergoing or requires bone or soft tissue reparative therapy. In some embodiment, an osteogenic composition may be made using an autologous tissue sample derived from the same subject on whom the composition is ultimately used, thereby avoiding any potential for immunological rejection of the composition.

The biological sample may include whole blood, an enriched red blood cell preparation, a platelet rich preparation, a bone marrow aspirate, bone marrow cells, or any combination thereof. The osteogenic compositions may be used in combination with an appropriate pharmaceutical carrier system for therapeutic applications involving bone or soft tissue repair. Optionally, the osteogenic compositions prepared according to the methods set forth herein may be supplemented with a therapeutically effective amount of one or more growth factors, one or more antibiotics, one or more bone proteins, one or more analgesics, or various combinations thereof.

Turning to FIG. 1, a method for preparing a osteogenic composition from a blood sample may include obtaining a sample of whole blood from a subject. The whole blood may be mixed with a suitable anticoagulant to prevent it from coagulating. In one embodiment, an enriched preparation of red blood cells (RBC) may be prepared from the whole blood. Any suitable methods for enriching red blood cells from whole blood may be used. Such methods are widely known in the art and may include, for example, centrifuging whole blood such that the red blood cells are enriched in a first fraction, a second fraction contains the plasma, and a third fraction contains platelets. Optionally, the whole blood or enriched RBC preparation may be diluted in an appropriate aqueous medium. The aqueous medium may be an isotonic solution, a hypotonic solution, or substantially pure water.

A lysate containing one or more osteogenic agents and cellular debris may be prepared from the whole blood or enriched RBC preparation. One method for preparing of a lysate may include acidifying the whole blood or enriched RBC preparation. Acidification may be accomplished by adding to the sample an appropriate amount of an acid, such as, for example, a Lewis acid. In one non-limiting embodiment, acidification may include mixing the cells in the whole blood or enriched RBC preparation with a volume of a 0.15 N acid, such as HCl. Optionally, the acidified lysate may be neutralized by adding an appropriate about of a base or another alkaline compound such as sodium phosphate, such that the pH of the lysate is in the range of about 4 to 10. Advantageously, hemoglobin released from the lysed RBC precipitates in this pH range. An alternate method of preparing a lysate may include subjecting the whole blood or enriched RBC preparation to one or more freeze/thaw cycles. Other non-limiting methods for lysing cells may include contacting the cells with a detergent to disrupt the cell membrane, sonication, homogenizing the cells with a dounce homogenizer, or mechanically lysing the cells using a Waring Blender Polytron or a mortar and pestle.

The solid material present in the lysate, including the cellular debris and/or precipitated proteins, may be separated from the lysate such that solid material is in one fraction, and a mixture containing one or more osteogenic factors is in a separate fraction. Any suitable means of separating solid material dispersed in a liquid may be used.

Figure 2:
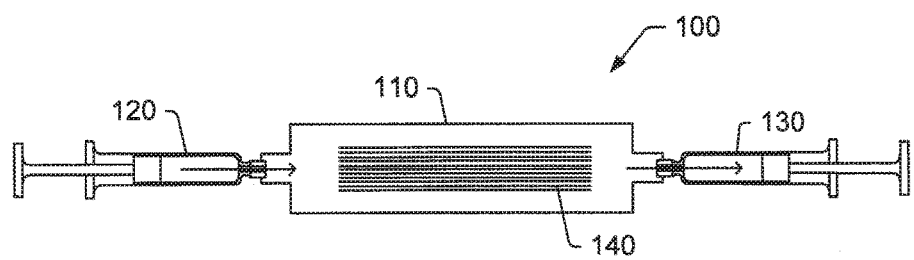
FIG. 2 shows a hollow fiber membrane filtration system for separating solid material from a lysate according to an embodiment.

In one non-limiting embodiment, the solid material may be separated from the lysate using a tangential flow hollow fiber filtration system equipped with a porous membrane having an average pore size of between about 0.05 to 5 microns. An exemplary tangential flow hollow fiber filtration system suitable for removing solid material from a lysate is shown in FIG. 2. Tangential flow hollow fiber filtration system 100 may include membrane cartridge 110 having syringe 120 coupled to the feeder end and syringe 130 coupled to the opposite end. A lysate containing dispersed solid material in combination with osteogenic factors is placed in syringe 120 and injected into the feeder end of membrane cartridge 110. The injected lysate is filtered through hollow tube fibers 140, which retains the solid material. The resulting filtrate, which is substantially free of solid material, is collected in syringe 130.

In an alternate embodiment, solid material may be separated from the lysate by centrifuging the lysate such that the solid material is compacted into a pellet fraction at the bottom of the centrifugation tube, and the osteogenic factors are contained in the supernatant fraction. Of course, it will be readily appreciated by a person having ordinary skill in the art that any other suitable method of removing solid material suspended in a liquid may be employed, without departing from the spirit and scope of the methods embodied herein.

Figure 3:
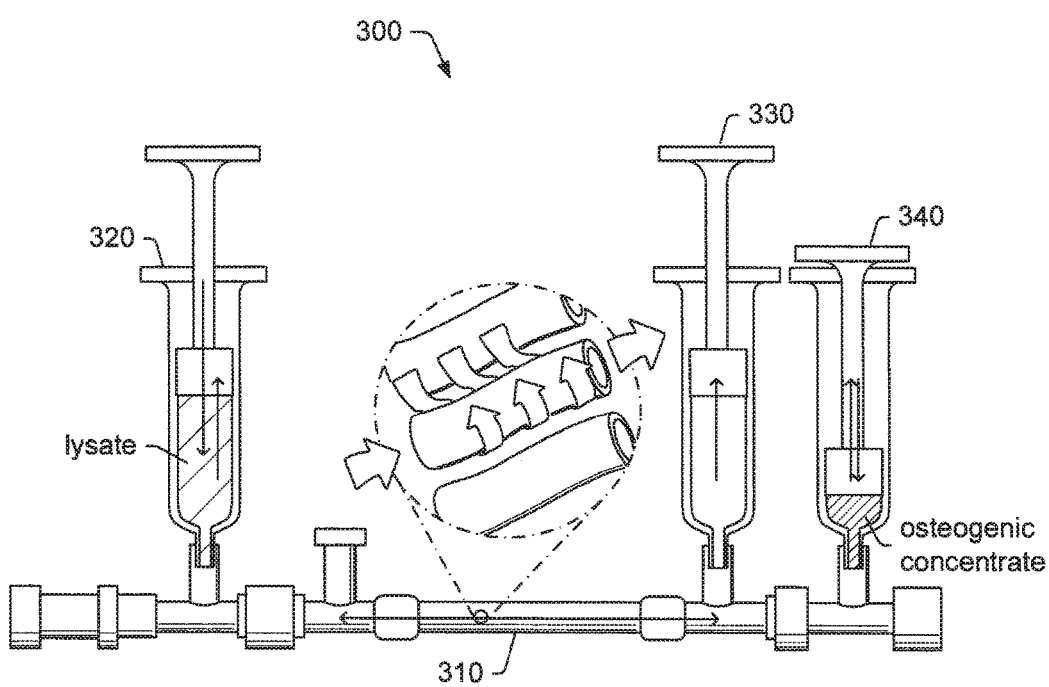
FIG. 3 shows a tangential flow hollow fiber membrane filtration system for concentrating a preparation containing osteogenic factors according to an embodiment.

Returning to FIG. 1, the fraction containing osteogenic factors may be concentrated. In one embodiment, the fraction may be concentrated using a tangential flow hollow fiber filtration system equipped with a porous membrane having a molecular weight cut off (MWCO) in the range of about 1 kD to about 100 kD, more preferably 5 kD to 50 kD, and most preferably 10 kD to 20 kD, such that the osteogenic factors are contained in the retentate. A suitable tangential-flow hollow fiber filtration system for concentrating osteogenic factors is depicted in FIG. 3. Tangential flow hollow fiber filtration system 300 may include membrane cartridge 310 having syringe 320 coupled to the feeder end, and syringes 330 and 340 coupled to the opposite end. A separated fraction containing osteogenic factors is placed in syringe 320, and injected into the feeder end of membrane cartridge 310. Filtered liquid is collected in syringe 330, and the retentate containing the osteogenic factors is collected in syringe 340. Optionally, the retentate may be subjected to one or more additional rounds of filtration by alternately engaging syringes 340 and 320.

The resulting concentrate is an osteogenic composition enriched for osteogenic factors, such as BMP-2, VEGF, PDGF and TGF-β, which may be applied to an appropriate pharmaceutical carrier medium suitable for use in bone and soft tissue reparative therapies. A pharmaceutical carrier medium may include, by way of non-limiting example, a block, a paste, cement mixture, powder, granule, putty, liquid, gel, or any combinations thereof, which are comprised of a ceramic, a polymer, a metal, allograft bone, autograft bone, demineralized bone matrix, or a mixture thereof.

Figure 4:
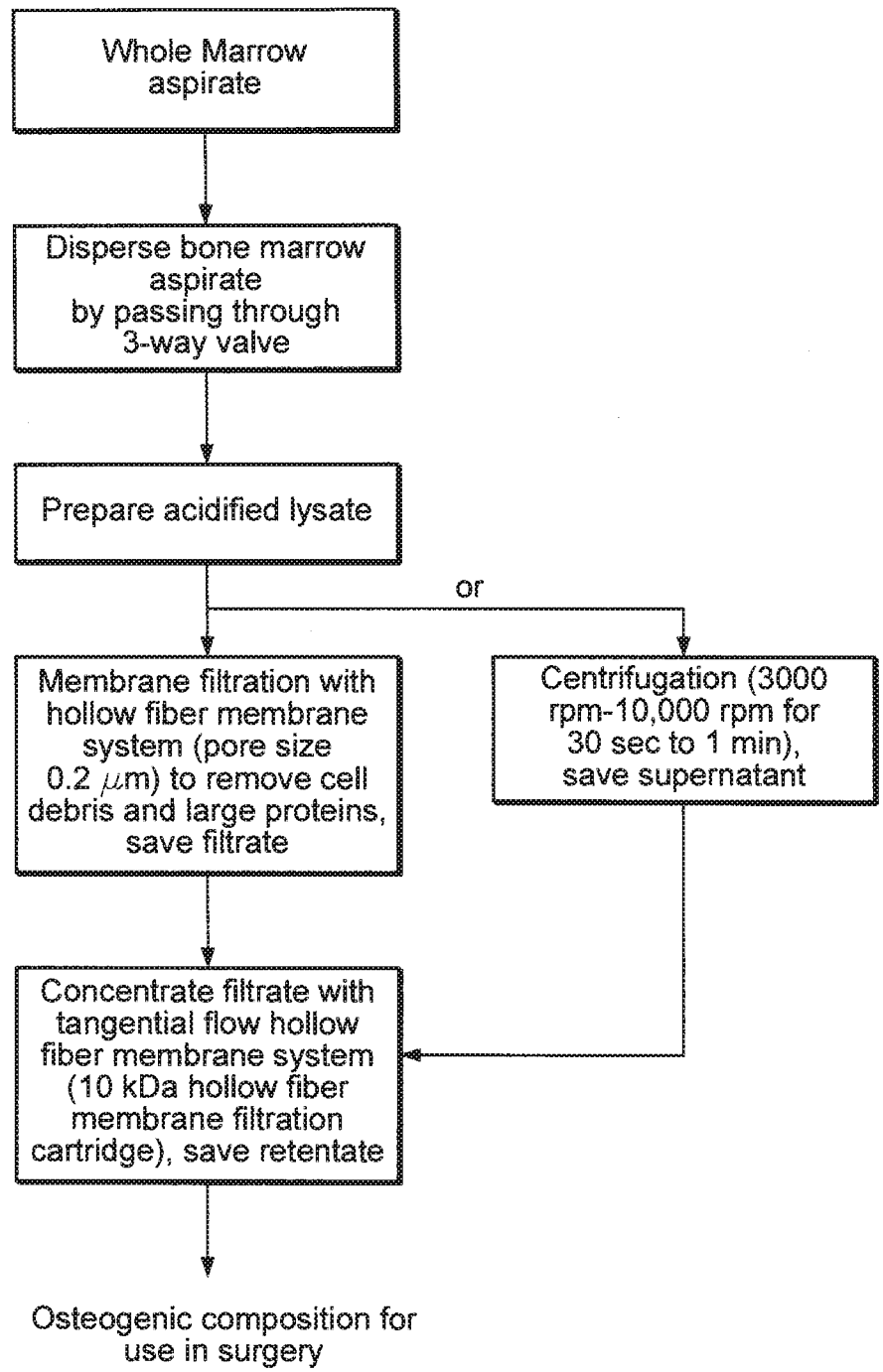
FIG. 4 is a flow chart depicting a method of preparing a osteogenic preparation from a bone marrow aspirate.

Turning now to FIG. 4, a method for preparing a osteogenic composition from bone marrow may include obtaining a bone marrow aspirate from a subject and mixing the aspirate with an aqueous medium optionally containing a suitable anticoagulant. The aqueous medium may be an isotonic solution, a hypotonic solution, or substantially pure water.

Figure 5:
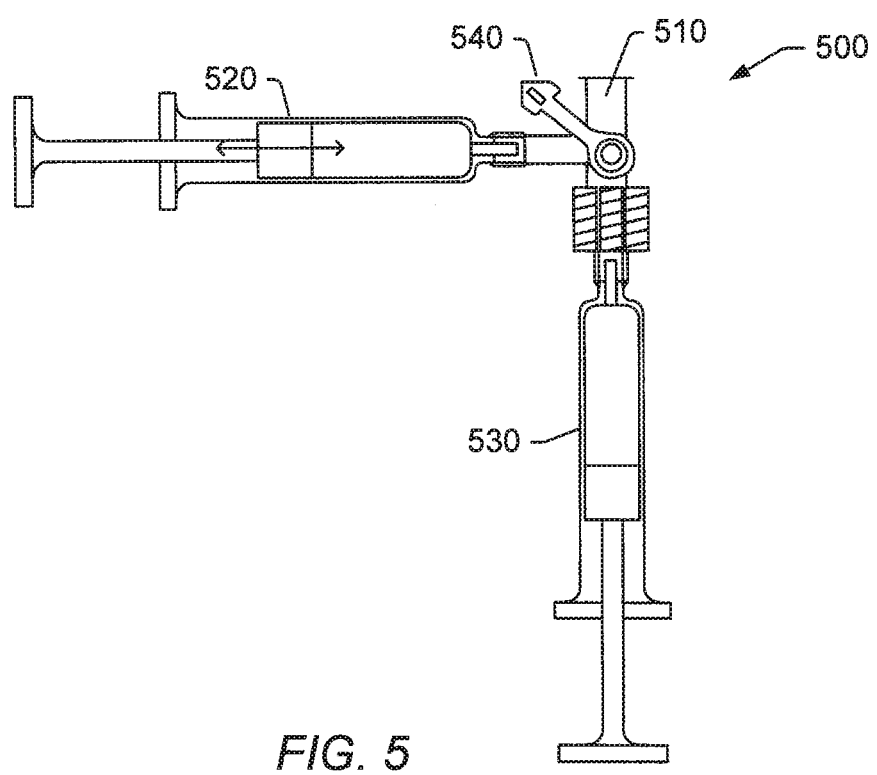
FIG. 5 depicts a three way valve for dispersing a bone marrow aspirate according to an embodiment.

In an embodiment, the aspirate may be dispersed such that cellular components present in the aspirate are suspended in the aqueous medium. Any suitable means of dispersing cells may be used. A method of dispersing cells in the aspirate may include repeatedly passing the aspirate and aqueous medium through a three way valve system, as shown in FIG. 5. Three way valve system 500 may include three way valve 510 having syringe 520 coupled to one port and syringe 530 coupled to another port. Valve 540 may be engaged to permit fluid communication between syringes 520 and 530. Syringes 520 and 530 may be alternately engaged so that the cells present in the aspirate are suspended in the aqueous medium.

Returning to FIG. 4, a lysate containing one or more osteogenic agents and cellular debris may be prepared from the suspended bone marrow cells. One method for preparing a lysate may include acidifying the cellular suspension. Acidification may be accomplished by adding to the suspension an appropriate amount of an acid, such as, for example, a Lewis acid. In one non-limiting embodiment, acidification may include mixing the suspended cells with one volume of a 0.15-1.5 N acid, such as HCl. An alternate method of preparing a lysate may include subjecting the suspension to one or more freeze/thaw cycles. Other non-limiting methods for lysing cells may include contacting the cells with a detergent to disrupt the cell membrane, sonication, homogenizing the cells with a dounce homogenizer, or mechanically lysing the cells using a Waring Blender Polytron or a mortar and pestle.

The solid material including the cellular debris may be separated from the lysate such that solid material is in one fraction, and a mixture containing one or more osteogenic factors is in a separate fraction. Any suitable means of separating solid material dispersed in a liquid may be used.

In one non-limiting embodiment, the solid material may be separated from the lysate using a tangential flow hollow fiber filtration as described above and shown in FIG. 2. The resulting filtrate, which is substantially free of solid material and is enriched for osteogenic agents, is collected in a syringe.

In an alternate embodiment, solid material may be separated from the lysate by centrifuging the lysate such that the solid material is compacted into a pellet at the bottom of the centrifugation tube, and the osteogenic factors are contained in the supernatant. Of course, it will be readily appreciated by a person having ordinary skill in the art that any other suitable method of removing solid material suspended in a liquid may be employed, without departing from the spirit and scope of the methods embodied herein.

Returning to FIG. 4, the fraction containing osteogenic factors may be concentrated. The fraction may be concentrated using a tangential flow hollow fiber filtration system equipped with a porous membrane having a molecular weight cut off (MWCO) in the range of about 1 kD to about 100 kD, more preferably 5 kD to 50 kD, and most preferably 10 kD to 20 kD, as described above and incorporated herein.

The resulting concentrate is a composition enriched for osteogenic factors, such as BMP-2, VEGF, PDGF and TGF-β, which may be applied to an appropriate pharmaceutical carrier medium suitable for use in bone and soft tissue reparative therapies. A pharmaceutical carrier medium may include, by way of non-limiting example, a block, a paste, cement mixture, powder, granule, putty, liquid, gel, or any combinations thereof, which are comprised of a ceramic, a polymer, a metal, allograft bone, autograft bone, demineralized bone matrix, or a mixture thereof.

Figure 6:
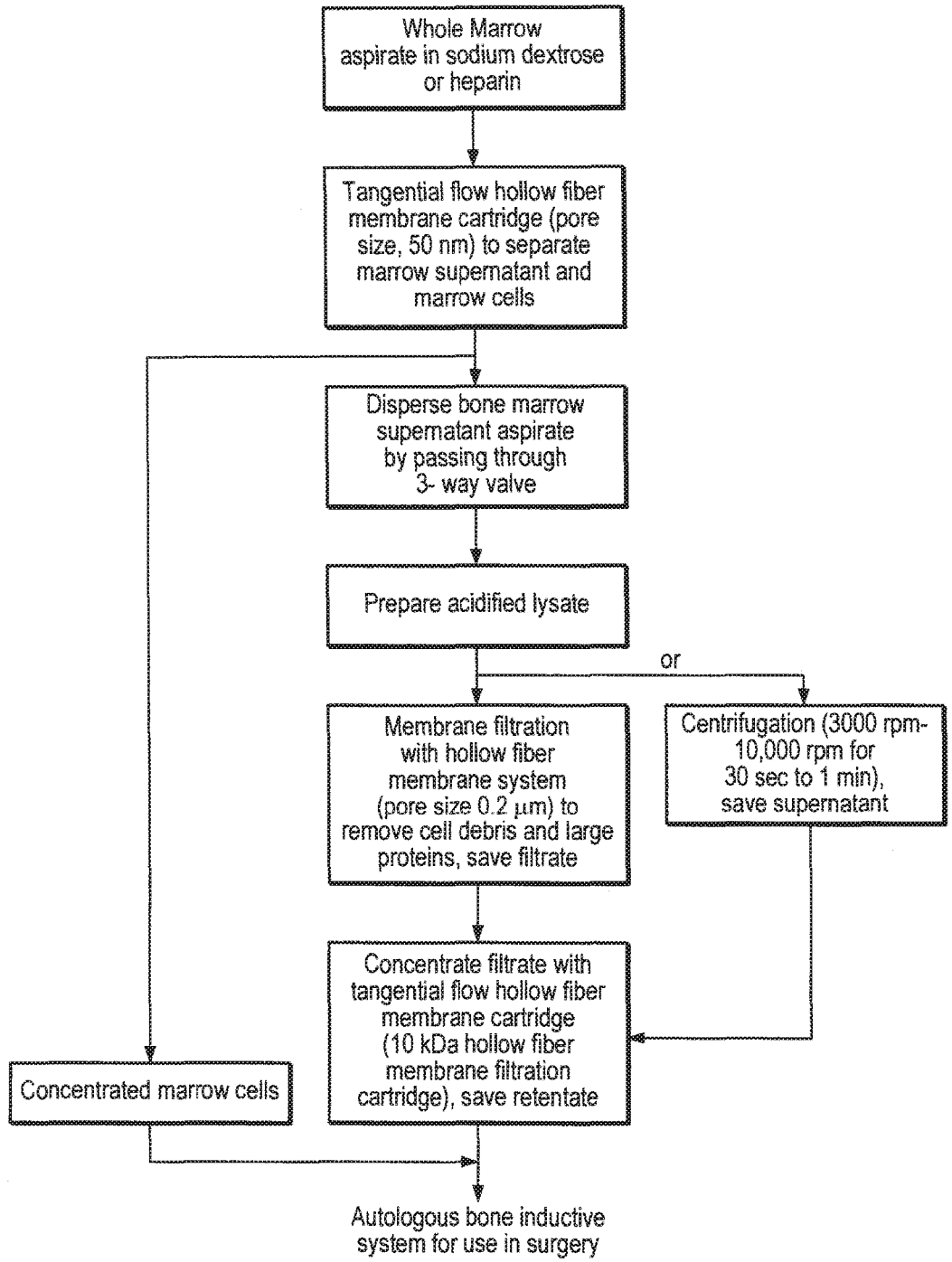
FIG. 6 is a flow chart depicting a method of preparing an autologous bone induction system containing bone marrow cells and an osteogenic composition.

Turning now to FIG. 6, a method for preparing an autologous osteogenic composition containing bone marrow cells and osteogenic factors dispersed in an aqueous medium may include obtaining a bone marrow aspirate from a subject and mixing the aspirate with an aqueous medium containing a suitable anticoagulant. The aqueous medium may be an isotonic solution, a hypotonic solution, or substantially pure water.

The bone marrow aspirate is dispersed in the aqueous medium as previously described. The dispersed cells may be collected by passing the suspension through an appropriate filtration system such that the bone marrow cells are in one fraction, and the suspension medium is in a separate fraction. One such filtration system may include the use of a tangential flow hollow fiber filtration system as described above, which is equipped with a porous membrane having an average pore size of about 50 nm to 0.5 microns. The retentate fraction contains bone marrow cells and the filtrate fraction contains the aqueous medium in which the cells were dispersed.

The collected cells are divided into at least two portions. One portion of cells may be set aside and another portion of cells may be processed as described above, such that a concentrate enriched for osteogenic factors is produced. The portion of cells that was set aside may be admixed with the concentrate to produce an autologous bone induction system containing a subject's bone marrow cells suspended in an aqueous medium enriched for osteogenic factors, such as BMP-2, VEGF, PDGF and TGF-β. The autologous bone induction system may be applied to an appropriate pharmaceutical carrier medium suitable for use in bone and soft tissue reparative therapies.

Optionally, any of the osteogenic compositions described above may be supplemented with a therapeutically effective amount of one or more pharmacologically active agents. A pharmacologically active agent may include, by way of non-limiting example, one or more growth factors, one or more antibiotics, one or more bone proteins, one or more analgesics, or various combinations thereof.

What constitutes a therapeutically effective amount of a pharmacologically active agent will of course vary depending on the identity of the agent, the physiological context in which the agent is being employed, and the magnitude of the desired response. The determination of a therapeutically effective dosage of a pharmaceutical agent is well within the skill level of an ordinary practitioner of the art. General guidance in determining effective dose ranges may be found, for example, in the publications of the International Conference on Harmonisation and in REMINGTON'S PHARMACEUTICAL SCIENCES, chapters 27 and 28, pp. 484-528 (Mack Publishing Company 1990), which is incorporated by reference as though fully set forth herein.

Non-limiting examples of suitable growth factors include osteogenin, Insulin-like Growth Factor (IGF)-1, IGF-II, TGF-β1, TGF-β2, TGF-β3, TGF-β4, TGF-β5, osteoinductive factor (OIF), basic Fibroblast Growth Factor (bFGF), acidic Fibroblast Growth Factor (aFGF), Platelet-Derived Growth Factor (PDGF), vascular endothelial growth factor (VEGF), Growth Hormone (GH), growth and differentiation factors (GDF)-5 through 9, osteogenic protein-I (OP-1) and any one of the many known bone morphogenic proteins (BMPs), including but not limited to BMP-1, BMP-2, BMP-2A, BMP-2B, BMP-3, BMP-3b, BMP-4, BMP-5, BMP-6, BMP-7, BMP-8, BMP-8b, BMP-9, BMP-10, BMP-11, BMP-12, BMP-13, BMP-14, BMP-15. The growth factors may be isolated from recombinant sources or may be purified from a biological sample. Optionally, a growth factor composition may also include one or more agents that support the formation, development and growth of new bone, and/or the remodeling thereof. Typical examples of compounds that function in such a supportive manner include, though are not limited to, extracellular matrix-associated bone proteins (e.g., alkaline phosphatase, osteocalcin, bone sialoprotein (BSP) and osteocalcin in secreted phosphoprotein (SPP)-1, type I collagen, fibronectin, osteonectin, thrombospondin, matrix-gla-protein, SPARC, alkaline phosphatase and osteopontin).

Suitable bone proteins may include one or more compounds that support the formation, development and growth of new bone, and/or the remodeling thereof. Bone proteins suitable for use in osteogenic composition may include, though are not limited to, alkaline phosphatase, osteocalcin, bone sialoprotein (BSP) and osteocalcin in secreted phosphoprotein (SPP)-1, type I collagen, type IV collagen, fibronectin, osteonectin, thrombospondin, matrix-gla-protein, SPARC, alkaline phosphatase and osteopontin. One or more bone proteins may be included in an osteoinductive composition.

Analgesics suitable for admixing with a osteogenic compositions may include, but are not limited to, norepinephrine, bupivacaine, ropivacaine, 2-chloroprocaine, lidocaine, mepivacaine, ropivacaine, mepivacaine, benzocaine, tetracaine, dibucaine, cocaine, prilocaine, dibucaine, procaine, chloroprocaine, prilocaine, mepivacaine, etidocaine, tetracaine, xylocaine, morphine, fentanyl, alphaxalone and active analogs, 5-alpha-pregnane-3 alpha-21-diol-20-one (tetrahydro-deoxycorticosterone or THDOC), allotetrahydrocortisone, dehydroepiandrosterone, benzodiapenes, nifedipine, nitrendipine, verapamil, aminopyridine, benzamil, diazoxide, 5,5 diphenylhydantoin, minoxidil, tetrethylammonium, valproic acid, aminopyrine, phenazone, dipyrone, apazone, phenylbutazone, clonidine, taxol, colchicines, vincristine, vinblastine, levorphanol, racemorphan, levallorphan, dextromethorphan, cyclorphan, butorphanol, codeine, heterocodeine, morphinone, dihydromorphine, dihydrocodeine, dihydromorphinone, dihydrocodeinone, 6-desoxymorphine, heroin, oxymorphone, oxycodone, 6-methylene-dihydromorphine, hydrocodone, hydromorphone, metopon, apomorphine, normorphine, N-(2-phenylethyl)-normorphine, etorphine, buprenorphine, phenazocine, pentazocine and cyclazocine, meperidine, diphenoxylate, ketobemidone, anileridine, piminodine, fentanil, ethoheptazine, alphaprodine, betaprodine, 1-methyl-4-phenyl-1,2,5,6-tetrahydropyridine (MPTP), loperamide, sufentanil, alfentanil, remifentanil, lofentanil, 6,7-benzomorphans, ketazocine, aryl-acetamides, U-50,488, spiradoline (U-62,066), enadoline (CI-977), asimadoline, EMD-61753, naltrexone, naltrindole.

Antibiotics suitable for admixing with a osteogenic compositions may include, but are not limited to, tylosin tartrate, tylosin, oxytetracycline, tilmicosin phosphate, ceftiofur hydrochloride, ceftiofur sodium, sulfadimethoxine cefamandole, tobramycin, penicillin, cefoxitin, oxacillin, vancomycin, cephalosporin C, cephalexin, cefaclor, cefamandole, ciprofloxacin, bisphosphonates, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione.

In some embodiments, osteogenic compositions prepared in accordance with methods described above may optionally be applied to a pharmaceutical carrier medium in a dosage form suitable for application to a bone defect. Such a dosage form may include injectable compositions, either as liquid solutions or suspensions, although solid forms suitable for suspension in a liquid prior to injection also may be prepared. In other embodiments, the pharmaceutical composition may be non-injectable.

In some embodiments, a suitable pharmaceutical carrier medium may include a synthetic material, a natural material, or both. In some embodiments, a pharmaceutical carrier medium may include biocompatible material that facilitates, permits, or enhances the laying down of new bone matrix, bone growth and/or bone ingrowth. A pharmaceutical carrier medium may include ceramics, such as calcium sulfate or calcium phosphate, polymers, metals, allograft bone, autologous bone, demineralized bone matrix, or any mixture thereof. In some embodiments, a pharmaceutical carrier medium may be in the form of a block, paste, cement, powder, granule, putty, gel, or so forth. In certain embodiments, a pharmaceutical carrier medium may breaks down over time when placed in the body. A pharmaceutical carrier medium may be a dust, powder, granule, chip, putty, tablet, mixture thereof.

In some embodiments, a pharmaceutical carrier medium may be in the form of a paste, which is delivered to a tissue in a subject having need thereof. The paste may substantially harden over time. The paste may include ceramics, such as calcium sulfate or calcium phosphate, polymers, metals, allograft bone, autograft bone, demineralized bone matrix, or any mixture thereof. In an embodiment, an osteogenic composition may be mixed with the paste such that the composition is evenly distributed in the paste. In an alternate embodiment, an osteogenic composition may be applied to a surface of the paste and absorbed therein. In yet a further embodiment, the paste may be applied to a bone, and the osteogenic composition is applied in situ.

In some embodiments, a pharmaceutical carrier medium may be substantially solid. At least a portion of the solid carrier medium may be porous. The solid carrier medium may have any shape. The solid carrier medium may include ceramics, such as calcium sulfate or calcium phosphate, polymers, metals, allograft bone, autologous bone, demineralized bone matrix, or any mixture thereof. In an embodiment, an osteogenic composition may be applied to the surface a solid carrier medium and be absorbed therein. In an alternate embodiment, the solid carrier medium may be soaked in a solution containing the osteogenic composition. In a further alternate embodiment, an osteogenic composition may be applied to a solid carrier medium using pressure.

In some embodiments, a pharmaceutical carrier medium may include phosphate buffer, dextrose, salt, dextran 40, dextran 70, or a mixture or combination thereof. Further compositions contained in a pharmaceutical carrier medium may include aqueous solutions, non-toxic excipients, including salts, preservatives, buffers and the like. Aqueous carriers include water, alcoholic/aqueous solutions, saline solutions, parenteral vehicles such as sodium chloride, Ringer's dextrose, etc. Preservatives include antimicrobial agents, anti-oxidants, chelating agents and inert gases, although in specific embodiments the concentrate is used soon after concentration at the point-of-care. The pH and exact concentration of the various components in the pharmaceutical are adjusted according to well-known parameters.

A suitable pharmaceutical carrier medium may include any physiologically acceptable material that can be admixed with osteogenic composition and that that facilitates or does not hinder bone growth upon administration to a bone defect. A pharmaceutical carrier medium may include a synthetic material, a natural material, or both. In some embodiments, a pharmaceutical carrier medium may include one or more biocompatible materials that facilitate, permit, or enhance the laying down of new bone matrix, bone growth and/or bone ingrowth. A pharmaceutical carrier medium may include ceramics, such as calcium sulfate or calcium phosphate cements, polymers, metals, allograft bone, autologous bone, demineralized bone matrix, a mixture thereof. In some embodiments, a pharmaceutical carrier medium may be in the form of a block, paste, cement, powder, granule, putty, gel, or so forth. In certain embodiments, a pharmaceutical carrier medium may break down over time when placed in the body. A pharmaceutical carrier medium may be a dust, powder, granule, chip, putty, tablet, mixture thereof, and so forth.

In certain embodiments, a suitable pharmaceutical carrier medium may include a calcium phosphate cement (CPC) composition containing particles of calcium phosphate ceramic material which, when combined with a suitable setting liquid forms a self-setting composition that hardens to become calcium phosphate-based biocompatible solid mass. A variety of CPCs are known in the art and detailed descriptions thereof, as well as their method of manufacture may be found, for example, in the disclosures of U.S. Pat. Nos. 7,018,460; 6,994,726; 6,972,130; 6,960,249; 6,955, 716; 6,953,594; 6,929,692; 6,916,177; 6,908,506; 6,905, 516; 6,855,167; 6,849,275; 6,840,995; 6,821,528; 6,808, 561; 6,796,378; 6,793,725; 6,777,001; 6,730,324; 6,719, 993; 6,719,773; 6,716,216; 6,706,273; 6,706,067; 6,703, 038; 6,692,563; 6,670,293; 6,648,960; 6,642,285; 6,641, 587; 6,620,236; 6,616,742; 6,613,054; 6,599,516; 6,596, 338; 6,593,394; 6,592,513; 6,582,228; 6,558,709; 6,547, 866; 6,541,037; 6,537,589; 6,527,810; 6,495,156; 6,417, 247; 6,384,197; 6,379,453; 6,375,935; 6,338,752; 6,325, 992; 6,296,667; 6,241,734; 6,224,629; 6,214,368; 6,206, 957; 6,149,655; 6,139,578; 6,136,029; 6,117,456; 6,083, 229; 6,053,970; 6,051,061; 6,027,742; 6,018,095; 6,005, 162; 6,002,065; 5,997,624; 5,993,535; 5,980,625; 5,976, 234; 5,968,253; 5,964,932; 5,962,028; 5,954,867; 5,952, 010; 5,900,254; 5,891,558; 5,885,540; 5,866,155; 5,846, 312; 5,820,632; 5,782,971; 5,709,742; 5,697,981; 5,695, 729; 5,683,667; 5,683,496; 5,679,294; 5,605,713; 5,571, 493; 5,569,442; 5,545,254; 5,542,973; 5,534,244; 5,525, 148; 5,522,893; 5,503,164; 5,496,399; 5,460,803; 5,437, 857; 5,427,768; 5,338,356; 5,336,264; 5,281,265; 5,262, 166; 5,218,035; 5,178,845; 5,152,836; 5,149,368; 5,053, 212; and 4,373,217, all of which are expressly incorporated herein by reference.

All of the essential materials and reagents required for performing bone reparative therapy may be assembled together in a kit. When the components of the kit are provided in one or more liquid solutions, the liquid solution preferably is an aqueous solution, with a sterile aqueous solution being particularly preferred. In the kit, there may be an apparatus to collect a biological sample from a subject, at least one filter and/or filter apparatus, a pharmaceutical carrier medium, a utensil and/or platform to combine the cell concentrate and scaffold material, and/or a combination thereof.

EXAMPLES

The following will serve to illustrate, by way of one or more examples, systems and methods for preparing an osteogenic composition from a biological sample. The examples set forth below are non-limiting and are intended to be merely representative of various aspects and features of certain embodiments. Although methods and materials similar or equivalent to those described herein may be used in the application or testing of the present embodiments, suitable methods and materials are described below.

Example 1

Preparation of an Autologous Osteogenic Composition from Whole Blood

Human whole blood was obtained commercially. Human whole blood was collected either in sodium citrate or acid citrate dextrose solution as anticoagulant. Red blood cell (RBC) concentration was determined and blood was diluted with PBS so the RBC density of was about 0.5 to 2 million cells per µL. The cells were lysed with one volume of 0.15 N hydrochloric acid for 5 min. The resulting lysate was neutralized with 0.5 volume of 0.3 N sodium hydroxide to pH 4 to 6 to precipitate hemoglobin and cell debris from solution.

A hollow fiber membrane filtration tangential flow unit (such as the one set forth in FIG. 4) with a membrane pore size of 0.2 µm was used to separate hemoglobin precipitates and cell debris from the lysate containing osteogenic agents. Briefly, the lysate was drawn in to a first syringe and injected into a hollow fiber membrane filtration unit such as is shown in FIG. 4. In this filtration step, cell debris and hemoglobin precipitates were retained inside the hollow fiber membrane, whereas small protein molecules like osteogenic growth factors and water can pass through membrane pores and be collected in a second syringe coupled to the opposite end of the filtration unit.

Alternatively, solid material may be separated from the lysate by centrifugation at 3000 to 10,000 rpm for 30 seconds to 1 min. After the clarification step, a clear filtrate or supernatant is obtained.

The osteogenic agents contained in the resulting composition were concentrated using a tangential flow membrane filtration cartridge (such as the one set forth in FIG. 5) equipped with a 10 kDa molecular weight cut off. As shown in FIG. 5, three syringes were attached to the tangential flow membrane filtration cartridge coupled to three syringes, as describe above in detail. The filtrate obtained from the previous step was place in a syringe, and the other two syringes are empty. The filtrate containing osteogenic factors was injected into filtration cartridge and a second syringe. By alternately pressing the first and second syringes back and forth for about 5 to 10 min, a concentrate containing osteogenic agents accumulate in the second in syringe and excess aqueous medium was collected in the remaining syringe and then discarded. The volume was brought down to ⅕ to 1/10 of initial volume of whole blood. The concentration of osteogenic agents (e.g. TGF-β1, BMP-2, PDGF-AB and VEGF) present in the final concentrate was measured by Enzyme linked ImmunoSorbent assay (ELISA).

Results

In the above procedure, osteogenic composition was prepared from human blood samples collected from three donors. Growth factor concentrations were measured by ELISA, and the results are listed in Table 1.

Table 2 lists the growth factors (VEGF, PDGF-AB, TGF-β1) concentrations obtained in a separate experiment, where the whole blood was replaced with an enriched RBC preparation derived from whole blood.

Table 3 lists the growth factor (VEGF, PDGF-AB, TGF-β1) concentrations obtained in a separate experiment, where the whole blood taken from five donors.

Table 4 lists growth factor (VEGF, PDGF-AB, TGF-β1) concentrations obtained in a separate experiment, where the acidified lysate was neutralized with the indicated sodium phosphate buffer.

This study shows that an osteogenic composition having significant amounts of various osteogenic agents, including BMP-2, VEGF, PDGF, and TGF-13 can be prepared from a sample of whole blood or cellular preparations thereof.

TABLE 1

Bone inductive composition prepared from a sample of whole blood

| Sample | Age | Blood Type | VEGF (pg/ml) | PDGF-AB (pg/ml) | BMP-2 (pg/ml) | TGF-β1 (pg/ml) |
|---|---|---|---|---|---|---|
| Donor 1 | 32 | A | 535.8 | 11,687.0 | 662.8 | 19,582.2 |
| Donor 2 | 44 | O | 765.6 | 20,841.1 | 626.5 | 48,166.9 |
| Donor 3 | 23 | A | 765.6 | 12,224.1 | 699.1 | 15,575.0 |
| Mean | | | 689.0 | 14,917.4 | 662.8 | 27,774.7 |

TABLE 2

Bone inductive composition prepared from an enriched RBC sample

| Sample ID | Age | Blood Type | VEGF (pg/ml) | PDGF-AB (pg/ml) | BMP-2 (pg/ml) | TGF-β1 (pg/ml) |
|---|---|---|---|---|---|---|
| Donor 4 | 41 | A | 207.6 | 13,459.4 | 153.3 | 45,546.0 |
| Donor 5 | 47 | O | 306.6 | 10,749.3 | 221.7 | 60,746.5 |
| Donor 6 | 36 | B | 257.1 | 23,726.7 | 149.6 | 90,755.3 |
| Donor 7 | 23 | O | 396.3 | 12,104.3 | 733.6 | 55,352.8 |
| Donor 8 | 47 | O | 454.9 | 14,553.9 | 256.8 | 74,819.3 |
| Mean | | | 324.5 | 14,918.7 | 303.0 | 65,444.0 |

TABLE 3

Bone inductive composition prepared from 5 blood samples

| Sample ID | Age | Blood Type | VEGF (pg/ml) | PDGF-AB (pg/ml) | BMP-2 (pg/ml) | TGF-β1 (pg/ml) |
|---|---|---|---|---|---|---|
| Donor 4 | 41 | A | 530.3 | 33,648.5 | 0.0 | 133,618.9 |
| Donor 5 | 47 | O | 900.7 | 32,215.3 | 0.0 | 166,702.1 |
| Donor 6 | 36 | B | 912.2 | 42,248.1 | 0.0 | 178,909.2 |
| Donor 7 | 23 | O | 1,089.3 | 21,140.1 | 0.0 | 120,482.2 |
| Donor 8 | 47 | O | 1,669.0 | 26,352.0 | 0.0 | 169,400.8 |
| Mean | | | 1,020.3 | 31,120.8 | 0.0 | 153,822.6 |

TABLE 4

Bone inductive composition neutralized with sodium phosphate

| Osteogenic factor | 1.65M $Na_2HPO_4$ pH 8.7 | | 2.43M $Na_2HPO_4$ pH 6.7 | | 2.43M $Na_2HPO_4$ pH 10.3 | |
|---|---|---|---|---|---|---|
| | BMP-2 | TGF-β1 | BMP-2 | TGF-β1 | BMP-2 | TGF-β1 |
| Concentration (pg/ml) | 1,650 | 4,600 | 5,800 | 4,700 | 4,600 | 4,800 |

Example 2

Preparation of an Autologous Osteogenic Composition from Bone Marrow Aspirate

Bone marrow aspirate was collected from the iliac crest of a New Zealand White rabbit, and supplemented with sodium citrate solution as anti-coagulant. An osteogenic composition was prepared from the bone marrow according to the procedure set forth in FIG. 4.

Whole marrow aspirate was first dispersed through a 3-way valve (shown in FIG. 5) for 5 to 10 passes using two syringes. The dispersed aspirate was collected in a syringe and lysed by adding an equal volume of 1.5 N HCl to the dispersion. The acidified dispersion was incubated at room temperature for 5 min. The lysate was injected into a hollow fiber membrane filtration cartridge (see FIG. 7) with pore size of 0.2 μm to separate the precipitates and cell debris from the lysate containing osteogenic factors. In this filtration step, the cell debris and hemoglobin precipitates were retained inside of the hollow fiber membrane, only small protein molecules like osteogenic growth factors and water can pass through membrane pores and accumulated in a syringe. The filtrate was further concentrated by using a tangential flow hollow fiber membrane cartridge with MWCO 10 kDa as above. The concentration of TGF-P1 and BMP-2 present in the concentrate was measured by ELISA.

Results

Osteogenic growth factors concentrations prepared from New Zealand White rabbits are listed in Table 5. The BMP-2 concentration in preparation made from rabbit marrow was approximately 12 times that of the whole marrow aspirate. The TGF-β1 concentration was 2.8 times that of the whole marrow aspirate. This study shows that osteogenic factors can be prepared bone marrow aspirate.

TABLE 5

| Sample | BMP-2 pg/mL | TGF-β1 pg/mL |
|---|---|---|
| Rabbit Whole Marrow | 201.8 | 245288.2 |
| Rabbit Marrow Supernatant | 1384.8 | 610530.5 |
| Rabbit Marrow ABIS | 2586.2 | 675819.0 |

Example 3

Preparation of an Autologous Bone Induction Composition from a Whole Cell Bone Marrow Aspirate Whole marrow aspirate was obtained, and placed in PBS. A cellular dispersion was prepared from the aspirate using a 3-way valve system. Bone marrow cells were collected from the dispersion as described above, using a tangential flow hollow fiber membrane cartridge equipped with membrane having a pore size of 50 nm. Collected bone marrow cells were divided into two portions. One portion of cells was set aside, and the other portion of cells was processed as described in Example 2 to produce a concentrate containing osteogenic agents. The concentrate was then mixed with the portion of bone marrow cells that was set aside, yielding an autologous osteogenic system.

The concentrations of TGF-β1 and BMP-2 in the osteogenic system was measured by ELISA. The volume of the final marrow preparation is normally reduced to ⅕ to ⅒ of initial volume of marrow aspirate. Concentrated growth factors, marrow cells, marrow supernatant can be either used separately or combined as an autologous bone induction system which includes autologous bone marrow cells for bone or soft-tissue repair surgery.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description to the invention. Changes may be made in the elements described herein without departing from the spirit and scope of the invention as described in the following claims. In addition, it is to be understood that features described herein independently may, in certain embodiments, be combined.

What is claimed is:

1. A method of preparing an osteogenic composition comprising:
    obtaining a biological sample, said biological sample comprising cells and one or more osteogenic agents, wherein the biological sample comprises a bone marrow aspirate;
    at least partially lysing the biological sample to produce a lysate, wherein lysing the biological sample comprises acidifying the biological sample by using 1.5N HCL to lyse the bone marrow aspirate, thereby forming an acidified lysate, said lysate comprising solid material and one or more osteogenic agents;
    neutralizing the acidified lysate;
    separating the lysate into a first fraction and a second fraction, said first fraction substantially comprising the one or more osteogenic agents, and said second fraction substantially comprising the solid material; and
    collecting said first fraction, thereby obtaining an osteogenic composition.

2. The method of claim 1, wherein the biological sample further comprises whole blood in combination with the bone marrow aspirate.

3. The method of claim 2, further comprising passing the bone marrow aspirate through a three-way valve system one or more times prior to lyse the bone marrow aspirate.

4. The method of claim 1, wherein neutralizing the acidified lysate comprises contacting the lysate with an alkaline composition.

5. The method of claim 1, wherein neutralizing the acidified lysate comprises contacting the lysate with a phosphate buffer.

6. The method of claim 1, wherein separating the lysate comprises applying the lysate to a tangential flow hollow fiber membrane filtration system such that the filtrate substantially comprises the first fraction and the retentate substantially comprises the second fraction.

7. The method of claim 1, wherein separating the lysate comprises centrifuging the lysate so that the supernatant substantially comprises the first fraction and the pellet substantially comprises the second fraction.

8. The method of claim 1, further comprising concentrating the first fraction.

9. The method of claim 8, wherein concentrating the first fraction comprises applying the first fraction to a hollow fiber membrane system.

10. The method of claim 9, wherein a molecular weight cut off of the membrane is about 10-20 kDa.

11. The method of claim 1, further comprising contacting the first fraction with a pharmaceutical carrier medium suitable for use in bone repair surgeries.

12. The method of claim 1, wherein the first fraction is an osteogenic composition enriched for osteogenic factors, including one or more of BMP-2, VEGF, PDGF and TGF-β, which is applied to an appropriate pharmaceutical carrier suitable for use in bone and soft tissue reparative therapies.

13. The method of claim 12, wherein the pharmaceutical carrier is in the form of a block, paste, cement, powder, granule, putty, liquid, gel, or a combination thereof, which is comprised of a ceramic, a polymer, a metal, allograft bone particles, autograft bone particles, demineralized bone matrix particles, or a mixture thereof.

14. A method of preparing an osteogenic composition from bone marrow comprising:
    obtaining a bone marrow aspirate from a subject;
    dispersing the bone marrow aspirate;
    lysing the cells in the dispersed bone marrow aspirate, wherein lysing the cells comprises acidifying the dispersed bone marrow aspirate by using 1.5 N HCL to lyse the cells, thereby forming an acidified lysate;
    neutralizing the acidified lysate;
    separating the lysate into a first fraction and a second fraction, said first fraction comprising one or more osteogenic agents present in the bone marrow, and said second fraction comprising solid material; and
    collecting said first fraction, thereby obtaining an osteogenic composition.

15. The method of claim 14, wherein the bone marrow comprises an autologous bone marrow aspirate obtained from a patient.

16. The method of claim 14, wherein dispersing the bone marrow aspirate comprises passing the bone marrow aspirate through a three-way valve system.

17. The method of claim 14, wherein neutralizing the acidified lysate comprises contacting the lysate with an alkaline composition.

18. The method of claim 14, wherein neutralizing the acidified lysate comprises contacting the lysate with a phosphate buffer.

19. The method of claim 14, wherein separating the lysate comprises passing the lysate through a hollow fiber membrane system such that the filtrate substantially comprises the first fraction and the retentate substantially comprises the second fraction.

20. The method of claim 14, wherein separating the lysate comprises centrifuging the lysate such that supernatant substantially comprises the first fraction and the pellet substantially comprises the second fraction.

21. The method of claim 14, further comprising concentrating the first fraction.

22. The method of claim 21, wherein concentrating the first fraction comprises applying the first fraction to a hollow fiber membrane system.

23. The method of claim 14, further comprising contacting the first fraction with a pharmaceutical carrier suitable for use in bone repair surgeries.

24. A method of preparing an autologous osteogenic composition from bone marrow comprising:
- obtaining a bone marrow aspirate from a subject;
- dispersing the bone marrow aspirate;
- collecting at least a portion of the bone marrow cells in the dispersed bone marrow aspirate, and dividing the bone marrow cells into at least a first portion and a second portion;
- lysing the cells in the first portion to produce a lysate, wherein lysing the cells comprises acidifying the bone marrow cells in the first portion by using 1.5 N HCL to lyse the cells, thereby forming an acidified lysate;
- neutralizing the acidified lysate;
- separating the lysate into a first fraction and a second fraction, said first fraction comprising one or more osteogenic agents present in the bone marrow, and said second fraction comprising solid material; and
- collecting said first fraction, thereby obtaining an autologous osteogenic composition.

* * * * *